(12) United States Patent
Keitel

(10) Patent No.: US 10,583,259 B2
(45) Date of Patent: Mar. 10, 2020

(54) INJECTION DEVICE

(71) Applicant: Haselmeier AG, St. Gallen (CH)

(72) Inventor: Joachim Keitel, Esslingen (DE)

(73) Assignee: Haselmeier AG, St. Gallen (CH)

( * ) Notice: Subject to any disclaimer, the term of this patent is extended or adjusted under 35 U.S.C. 154(b) by 870 days.

(21) Appl. No.: 15/230,259

(22) Filed: Aug. 5, 2016

(65) Prior Publication Data

US 2016/0339181 A1 Nov. 24, 2016

Related U.S. Application Data

(63) Continuation of application No. PCT/EP2015/000206, filed on Feb. 3, 2015.

(30) Foreign Application Priority Data

Feb. 5, 2014 (DE) .................... 20 2014 001 135 U

(51) Int. Cl.
*A61M 5/315* (2006.01)
*A61M 5/24* (2006.01)

(52) U.S. Cl.
CPC .......... *A61M 5/31585* (2013.01); *A61M 5/24* (2013.01); *A61M 5/3155* (2013.01); *A61M 5/3156* (2013.01); *A61M 5/31551* (2013.01); *A61M 5/31593* (2013.01)

(58) Field of Classification Search
CPC ............ A61M 5/31551; A61M 5/3156; A61M 5/31585; A61M 5/3155
See application file for complete search history.

(56) References Cited

U.S. PATENT DOCUMENTS

| 5,114,406 A | 5/1992 | Gabriel et al. |
| 5,626,566 A * | 5/1997 | Petersen ........... A61M 5/31551 |
| | | 222/309 |
| 7,090,662 B2 | 8/2006 | Wimpenny et al. |
| 7,686,786 B2 * | 3/2010 | Moller ............. A61M 5/14566 |
| | | 604/134 |

(Continued)

FOREIGN PATENT DOCUMENTS

| RU | 79426 U1 | 1/2009 |
| SU | 1057040 A1 | 11/1983 |

(Continued)

OTHER PUBLICATIONS

International Search Report dated Apr. 14, 2015 of international application PCT/EP2015/000206 on which this application is based.

*Primary Examiner* — Andrew M Gilbert
(74) *Attorney, Agent, or Firm* — Walter Ottesen, P.A.

(57) ABSTRACT

An injection device includes a housing and a setting part configured to, in relation to said housing, rotate in a first rotational direction when an amount of injection fluid to be dispensed is being set. The setting part rotates in a second rotational direction counter to the first rotational direction when the injection fluid is pressed out of the injection device. A latching unit defines at least one latching position of the setting part and acts between the setting part and the housing. The latching unit is active at least when the amount of injection fluid to be dispensed is set and each of the latching positions has an unequivocal rotational position of the setting part in relation to the housing assigned thereto.

14 Claims, 7 Drawing Sheets

(56) References Cited

U.S. PATENT DOCUMENTS

| | | | |
|---|---|---|---|
| 7,955,303 B2* | 6/2011 | Burren | A61M 5/24 604/136 |
| 8,747,367 B2 | 6/2014 | Keitel et al. | |
| 9,138,542 B2* | 9/2015 | Smith | A61M 5/20 |
| 9,408,978 B2 | 8/2016 | Plumptre et al. | |
| 2008/0306446 A1* | 12/2008 | Markussen | A61M 5/20 604/139 |
| 2009/0048561 A1 | 2/2009 | Burren et al. | |
| 2013/0096513 A1* | 4/2013 | Smith | A61M 5/20 604/211 |

FOREIGN PATENT DOCUMENTS

| | | |
|---|---|---|
| SU | 1634285 A1 | 3/1991 |
| WO | 2013/117332 A1 | 8/2013 |

\* cited by examiner

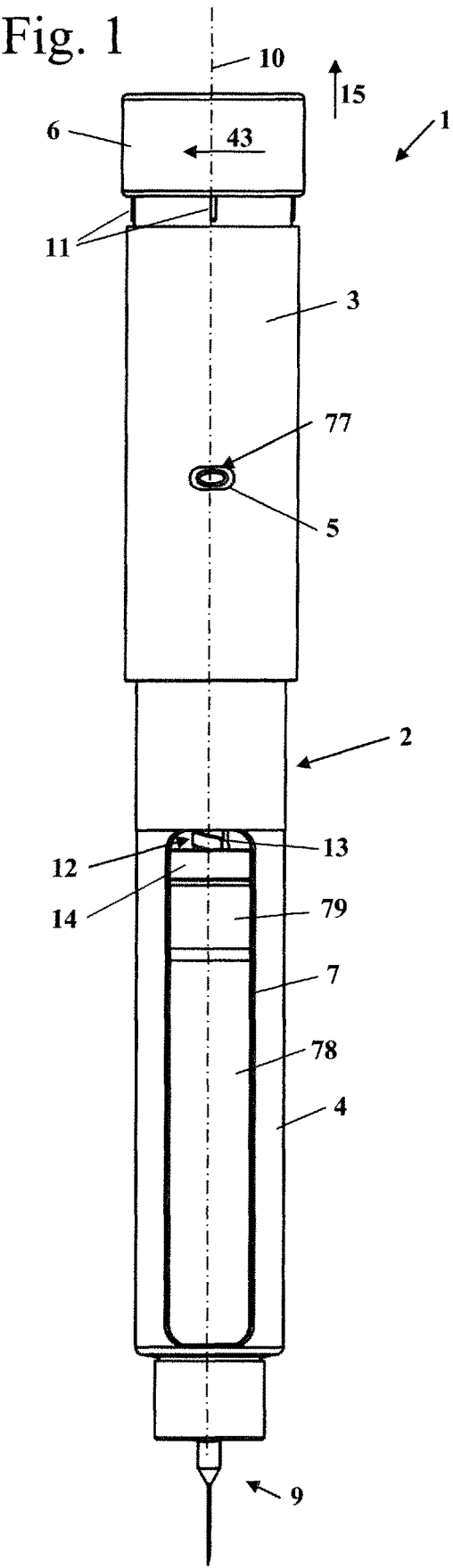
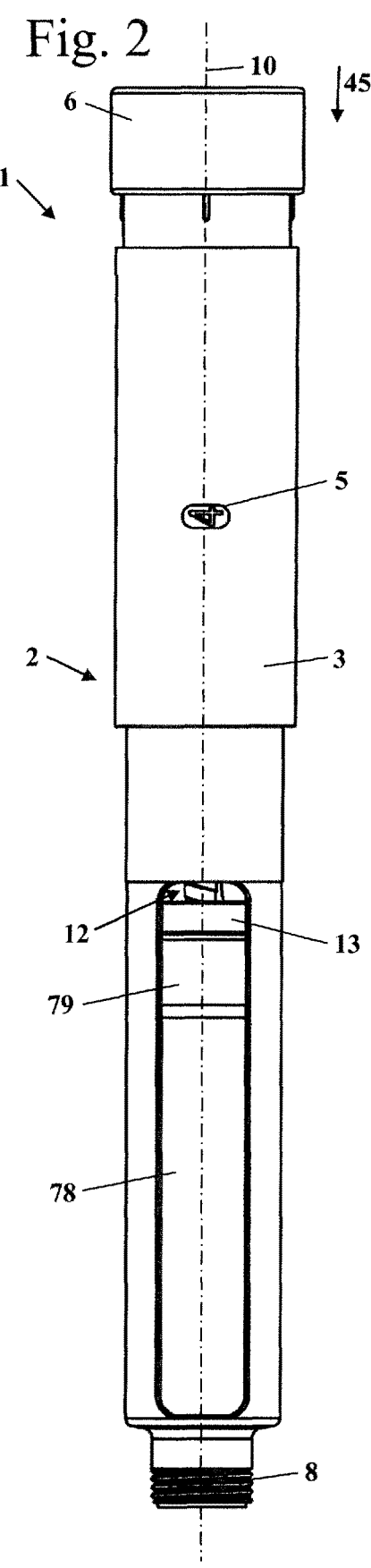

INJECTION DEVICE

CROSS REFERENCE TO RELATED APPLICATIONS

This application is a continuation application of international patent application PCT/EP2015/000206, filed Feb. 3, 2015, designating the United States and claiming priority from German application 20 2014 001 135.4, filed Feb. 5, 2014, and the entire content of both applications is incorporated herein by reference.

BACKGROUND OF THE INVENTION

An injection device which as a setting part has a graduated tube is known from U.S. Pat. No. 8,747,367. When setting an amount of injection fluid to be pressed or squeezed out, the graduated tube is moved in the distal direction. The graduated tube is moved in the opposite direction when the amount of injection fluid to be squeezed out or dispensed is being pressed out. The graduated tube is connected to the housing by way of a threaded connection such that the graduated tube, in addition to the movement in the distal or proximal direction, is also rotated in relation to the housing. Moreover, the injection device has a latching installation which acts between a threaded part and the housing. When setting the amount of injection fluid to be dispensed, the threaded part is rotated in relation to the housing. When the amount of injection fluid to be dispensed is being pressed out, the threaded part is guided in the axial direction in the housing such that the latching installation is not active when a dosage is being pressed out, there being no audible clicks of the latching installation.

The injection device known from U.S. Pat. No. 8,747,367 has fixed dosing increments. If and when, for example, amounts of 0.20 ml and 0.25 ml of injection fluid which are to be set for a therapy are required, then known injection devices are conceived such that dosing increments of at most 0.05 ml are settable. This means, on the one hand, that the user has to overcome a plurality of latching steps until he reaches the minimum dosage which is intended for the therapy. On the other hand, the amount of injection fluid which has to be discarded during the priming procedure is comparatively sizeable in the case of a minimum fixed dosing increment of 0.05 ml, for example. Therefore, significantly smaller dosing increments would be desirable for the priming procedure. However, this leads to a significantly increased number of latching positions which have to be overcome by the operator when setting the dosage.

SUMMARY OF THE INVENTION

It is an object of the invention to provide an injection device which enables a plurality of latching positions to be disposed at variable spacings.

The injection device of the invention defines a longitudinal center axis. The injection device includes: a housing; a setting part configured to, in relation to the housing, rotate in a first rotational direction when an amount of injection fluid to be dispensed is being set; the setting part being further configured to rotate in a second rotational direction counter to the first rotational direction when the injection fluid is being pressed out of the injection device; a latching unit defining at least one latching position of the setting part and configured to act between the setting part and the housing; the latching unit being configured to be active at least when the amount of injection fluid to be dispensed is being set; and, each of the at least one latching positions having an unequivocal rotational position of the setting part in relation to the housing assigned thereto.

Each latching position is assigned an unequivocal rotational position of the setting part in relation to the housing. On account thereof, the required latching positions may be disposed at variable mutual spacings. For example, an injection device which provides precisely three latching positions at 0.01 ml for the priming procedure, and at 0.20 ml and 0.25 ml for the dosages to be injected, could be provided for the exemplary therapy which has been described at the outset. Operating the injection device is significantly simplified on account thereof.

In the case of the injection device according to U.S. Pat. No. 8,747,367, the relative radial position of the threaded part in relation to the graduated tube is modified in the case of each injection. When a dosage is being set, the graduated tube and the threaded part are rotated in relation to the housing. When the amount of injection fluid to be dispensed is being pressed out, the graduated tube is rotated back while the threaded part is guided in a rotationally fixed and axially movable manner in the housing. On account thereof, the rotational position of the threaded part in the housing in the case of a predefined dosage to be set is not specified and may be modified in the case of each injection procedure. By contrast, the present invention provides that each latching position is assigned an unequivocal rotational position of the setting part in relation to the housing. On account thereof, the latching positions may be disposed at variable mutual spacings. For example, latching positions which are not assigned to any envisaged amounts of injection fluid may be dispensed with.

A simple construction results when at least one latching position is defined by at least one first latching element which is connected in a rotationally fixed manner to the housing, and at least one second latching element which is connected in a rotationally fixed manner to the setting part and which interacts with the first latching element. The latching elements here are always connected in a rotationally fixed manner to the housing or the setting part, respectively. On account of the fact that the setting part during the injection procedure is rotated back conjointly with the second latching element, it may be achieved in a simple manner that each latching position is assigned an unequivocal rotational position of the setting part in relation to the housing. Advantageously, the latching installation includes a latching part which, independently of the setting part, is axially displaceable. The latching part here is connected in a rotationally fixed manner to the housing. At least one first latching element is disposed on the latching part. In a first axial position of the latching part and of the setting part, at least one first and at least one second latching element define at least one latching position. In at least one second axial position of the latching part and of the setting part, the latching elements, independently of the rotational position of the setting part in relation to the latching part, are disengaged. The first axial position and the second axial position here are relative mutual positions of the latching part and of the setting part in the axial direction. The position of the latching part and of the setting part in relation to the housing may be variable here. On account of the latching elements being disengaged in the second axial position of the latching part and of the setting part, the setting part may be reset in relation to the latching part in the second axial position. The second axial position advantageously exists when the injection fluid is pressed out of the injection device. On account thereof, no clicks of the latching installation are audible when the injection fluid is being pressed out. The force required for pressing out the injection fluid may be minimized even in the case of latching positions which are clearly higher and perceptible when setting the amount of injection fluid to be dispensed.

Advantageously, the injection device has a spring which biases the latching part in the direction toward the first axial position. The spring is in particular a compression spring or a tension spring which exerts a force on the latching part in the direction of a longitudinal central axis of the injection device. In the absence of any force acting counter to the spring, the latching installation is active. The latching elements are advantageously aligned in the axial direction and act in the axial direction. At least one latching element prior to reaching a latching position is advantageously deflected in the direction of the longitudinal central axis of the injection device.

Advantageously, the latching installation in each latching position permits relative rotation of the setting part in relation to the housing in the first rotation direction and blocks the relative rotation in the second rotation direction. On account thereof, reverse rotation of a dosage that has once been set is not possible. However, it may also be provided that the latching installation is conceived such that latching positions may be skipped by the operator in the second rotation direction. The injection device in particular has a spring which acts between the setting part and the housing and which biases the setting part in the second rotation direction. The spring resets the setting part to the next lesser latching position when the setting part is not located in any latching position. The spring is a torsion spring in particular. The latching installation here is advantageously conceived such that the latching installation blocks the relative rotation of the setting part in the second rotation direction at that torque that is applied by the spring. However, it may be provided that the latching installation, by applying a higher torque, may be adjusted by the operator in the second rotation direction from one latching position to the next lesser latching position. Resetting in the case of an excessive dosage that has been erroneously set may be enabled by a corresponding layout of the latching installation and of the spring. By way of the spring, it may be prevented that the setting part remains static in a position between latching positions, so that an unintended amount of injection fluid is pressed out. The injection device advantageously has a first spring which biases the latching part in the direction toward the first axial position, and a second spring which biases the setting part in the second rotation direction. However, either only the first spring or only the second spring may also be provided.

Advantageously, the injection device has a coupling which in a first position connects the setting part in a rotationally fixed manner to an operating element, and which in a second position permits relative rotation of the setting part in relation to the operating element. Advantageously, when setting an amount of injection fluid to be dispensed, the coupling is in the first position, and, when the injection fluid is being pressed out of the injection device, the coupling is in the second position. On account thereof, operation in which the operating element when setting the amount of injection fluid to be dispensed is rotated conjointly with the setting part, and in which the operating element when the amount of injection fluid to be dispensed is being pressed out is displaced in the proximal direction, is possible. On account of the setting part, which is rotated in relation to the housing when the injection fluid is being pressed out, also being able to rotate in relation to the operating element, the operating element does not have to be rotated when the amount of injection fluid to be dispensed is being pressed out. Advantageously, when the amount of injection fluid to be dispensed is being pressed out, the operating element is guided along at least part of the displacement path thereof in a rotationally fixed manner in relation to the housing.

Adjustment of the coupling from the first to the second position is advantageously performed by displacing the operating element in the proximal direction. The latching part is advantageously coupled in the axial direction to the operating element in such a manner that movement of the operating element in the proximal direction causes movement of the latching part in the proximal direction. On account thereof, it is ensured that the latching installation is not active when the coupling is located in the second position, that is, when an injection is possible. A simple construction results when the latching part and the operating element are interconnected in an axially fixed manner and so as to be rotatable in relation to one another. On account thereof, a spring which biases the latching part in the axial direction also acts on the operating element. The spring advantageously acts on the operating element in the distal direction such that the operating element when initiating an injection has to be moved in the proximal direction, counter to the force of the spring.

A simple configuration of the coupling results when the coupling has a first toothing on the setting part which interacts with a second toothing on the operating element. Since the relative position of the operating element in relation to the setting part may be modified during operation, when the operating element is rotated in relation to the housing when setting the amount of injection fluid to be dispensed, but is guided in a rotationally fixed manner in relation to the housing during the injection procedure, the coupling has to enable a rotationally fixed connection between the operating element and the setting part in all theoretically possible rotational positions of the operating element and of the setting part in relation to one another. This may be achieved in a simple manner by a toothing of correspondingly fine configuration.

Advantageously, the setting part is connected by way of a first threaded connection to the housing, and when setting an amount of injection fluid to be dispensed, additionally to rotating in the first rotation direction, moves in the distal direction, and when a set amount of injection fluid is being pressed out, additionally to rotating in the second rotation direction, moves in the proximal direction. In one preferred embodiment, the distance along which the setting part is moved in the distal direction corresponds to the distance which has to be covered by a dosing piston of the injection device in order to press out the set amount of injection fluid. This is advantageous in particular when a spring which biases the setting part in the second rotation direction acts between the setting part and the housing. The rotation of the setting part in the second rotation direction, causing the set amount of injection fluid to be dispensed, here is advantageously caused by the spring such that pressing out the set amount of injection fluid is automatically performed once the latching position has been released.

In one preferred application, the injection fluid is located in a substantially cylindrical container made of glass which on one side is closed by a plug and on the other side by a sealing disk. The sealing disk is pushed against the container by a flange cap. Prior to injection fluid being able to be pressed out, the sealing disk has to be pierced by an injection needle. In order for injection fluid to be pressed out, the plug is displaced by way of a dosing piston of the injection device along the desired path, on account of which a corresponding amount of injection fluid is pressed out through the injection needle. The operating element is advantageously connected in a rotationally fixed manner to a feed part, wherein the feed part is connected by way of a second threaded connection to the dosing piston. The dosing piston is held in a rotationally fixed manner in relation to the housing. On account thereof, the feed part is moved by way of the second threaded connection in the distal direction when setting the amount of injection fluid to be dispensed. Since the feed part is connected in a rotationally fixed manner to the operating element when the amount of injection fluid to be dispensed is being pressed out, the feed part is not rotated when the amount of injection fluid to be dispensed is being pressed out, but is moved in the proximal direction only. On account thereof, the dosing piston is also pushed in the proximal direction and slides the plug of the cartridge. Advantageously, the setting part acts on the feed part in such a manner that movement of the setting part in the proximal direction causes movement of the feed part in the proximal direction. The first and the second threaded connections here may in particular be conceived such that the setting part, when setting the amount of injection fluid to be dispensed, covers at least the same distance as the feed part in the distal direction. It is preferably provided that the feed part and the setting part cover approximately the same distance in the distal direction.

BRIEF DESCRIPTION OF THE DRAWINGS

The invention will now be described with reference to the drawings wherein:

FIG. 1 shows a side view of an injection device prior to setting an amount of injection fluid to be dispensed;

FIG. 2 shows the injection device of FIG. 1, after setting an amount of injection fluid to be dispensed;

DESCRIPTION OF THE PREFERRED EMBODIMENTS OF THE INVENTION

Figure 3:
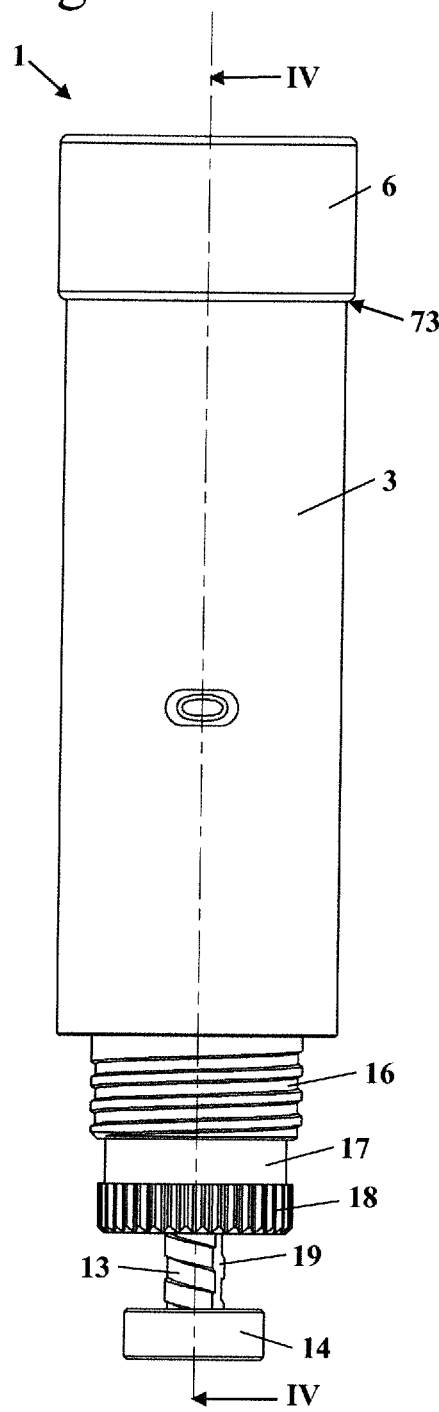
FIG. 3 shows a side view of the injection device of FIGS. 1 and 2, after injection fluid has been pressed out, wherein the holder for the cartridge has been removed.

An injection device 1 which serves for setting an envisaged amount of injection fluid and for pressing the latter out of a cartridge held in the injection device 1 is shown in FIGS. 1 and 2. The injection device 1 has a housing 2 which includes an upper housing part 3 and a holder 4 which is disposed on the upper housing part 3. The cartridge, which includes an advantageously transparent container 78 having injection fluid, and a plug 79 which is disposed in the container 78 and is advantageously visible from the outside, is disposed in the holder 4. The holder 4 in the embodiment has two viewing windows 7 which are disposed so as to be mutually opposite and through which the operator sees how much injection fluid is still contained in the container 78. A dosing piston 12 of the injection device 1 bears on the plug 79. The dosing piston 12 has a piston rod 13, a piston disk 14 being held thereon. The piston disk 14 of the dosing piston 12 bears on the plug 79 of the container 78 and presses out the injection fluid by displacing the plug 79 in the proximal direction. The proximal direction here refers to the injection direction, that is, the direction toward a receptacle for the injection needle, or that direction in which the injection fluid is pressed out of the container 78, respectively. The distal direction refers to the opposite direction, that is, away from the injection needle. The distal end of the injection device is that end that lies remote from an injection needle which is held on the injection device. "Proximal" refers to that side of the injection device that during an injection faces the injection site, "distal" referring to that side that lies remote from the injection site.

As is shown in FIGS. 1 and 2, the holder 4 on the proximal side thereof has an external thread 8 on which an injection needle 9 is fixed. Instead of the external thread 8, any other type of fastening installation for fixing the injection needle 9 to the holder 4 may also be provided. The injection needle 9 has been removed in FIG. 2, so that the external thread 8 is visible.

The injection device 1 on the distal end thereof has an operating element 6. As is also shown in FIG. 1, a plurality of longitudinal ribs 11 which run parallel to a longitudinal central axis 10 of the injection device 1 are disposed on the operating element 6, on that side that faces the upper housing part 3. Moreover, the upper housing part 3 has a clearance 5 through which a graduation 77 is visible, the latter indicating the set amount of injection fluid. No dosage has been set in the position of the injection device 1 shown in FIG. 1. In order for a dosage to be set, the operating element 6 in relation to the housing 2 has to be rotated in a first rotation direction 43 which in the embodiment corresponds to the clockwise direction. The operating element 6 here is moved in the distal direction, that is, in the direction of the arrow 15, in relation to the housing 2.

Figure 4:
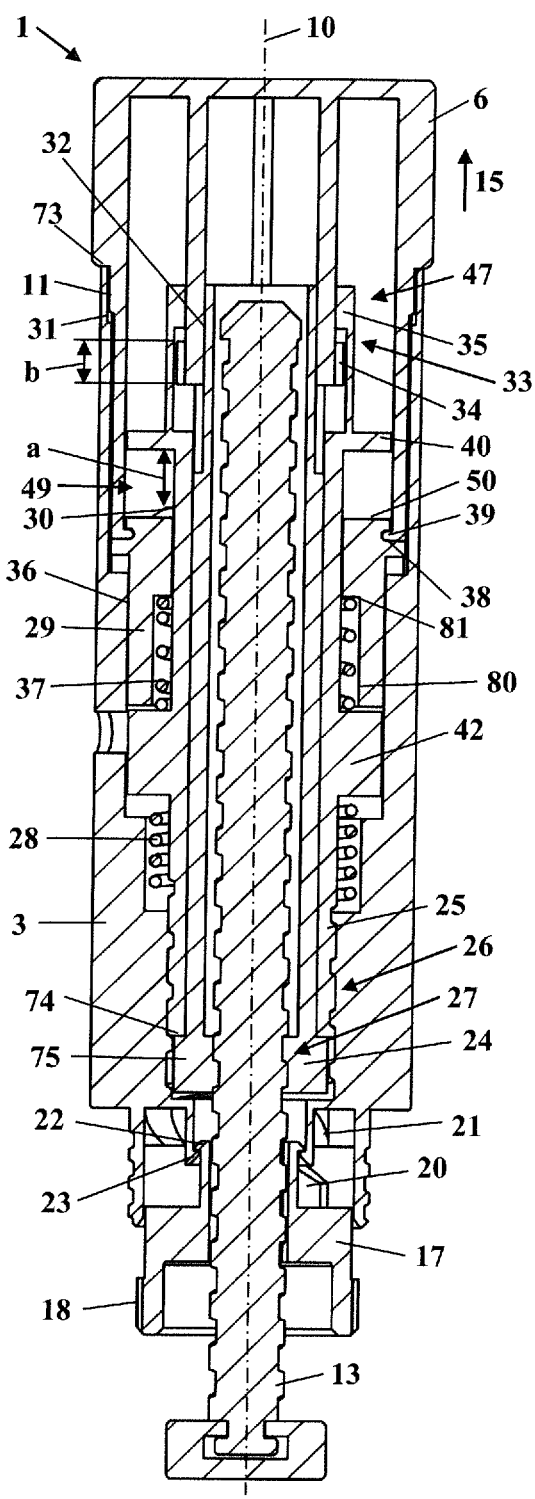
FIG. 4 shows a section along the line IV-IV in FIG. 3.

A dosage which in the embodiment is referred to by the numeral "4" has been set in the position shown in FIG. 2. In order for the set dosage to be pressed out, the operating element 6 has to be moved in the proximal direction, that is, in the direction of the arrow 45 in FIG. 2, in relation to the housing 2. Here, the operating element 6 is pushed by the operator in the proximal direction, counter to the force of a spring 37 (FIG. 4) which is yet to be described in more detail hereunder. The injection device 1 in FIG. 3 is shown in the position in which the operating element 6 has been displaced in the proximal direction up to a stop 73 which is formed between the operating element 6 and the upper housing part 3. As is also shown in FIG. 4, in this position of the operating element 6, the operating element 6 by way of the longitudinal ribs 11 which protrude into longitudinal grooves 31 of the upper housing part 3 is held in a rotationally fixed manner in relation to the housing 2. In order to be able to again set an amount of injection fluid to be dispensed, the operating element 6 has first to be moved in the distal direction in the direction of the longitudinal central axis 10, as is indicated by the arrow 15, until the longitudinal ribs 11 have emerged from the longitudinal grooves 31 and the operating element 6 is located in the position shown in FIG. 1. The movement of the operating element 6 in the distal direction is performed by virtue of the spring 37 which is shown in FIG. 4. Once the operating element 6 has been displaced in the distal direction by the spring 37, an amount of injection fluid to be dispensed may again be set by rotating the operating element 6 in the first rotation direction 43.

As is shown in FIGS. 3 and 4, the upper housing part 3 on the proximal end thereof has a thread 16 onto which the holder 4 may be screwed. A piston-rod guide 17 which on the external circumference thereof has a knurl 18 protrudes from the upper housing part 3 at the proximal end. The piston-rod guide 17 is connected in a rotationally fixed manner to the piston rod 13. To this end, the piston rod 13 on a longitudinal side has at least one bevel 19, a corresponding bevel of the piston-rod guide 17 engaging therein in a known manner. The piston-rod guide 17 is biased by a spring (not shown) to the position which is shown in FIGS. 3 and 4. If a container 78 is placed in the holder 4, and if the holder 4 is screwed onto the thread 16, the piston-rod guide 17 is moved by the container 78 in the distal direction. As is shown in FIG. 4, the piston-rod guide 17 has at least one ramp 20 which in the distal position of the piston-rod guide 17 interacts with at least one ramp 21 of the upper housing part 3 and, on account thereof, connects the piston-rod guide 17 in a rotationally fixed manner to the upper housing part 3. On account thereof, in the case of a fitted holder 4, the piston rod 13 is connected in a rotationally fixed manner to the upper housing part 3. As is also shown in FIG. 4, the piston-rod guide 17 has a latching periphery 22 which interacts with a latching periphery 23 of the upper housing part 3 and, on account thereof, holds the piston-rod guide 17 on the upper housing part 3, counter to the force of the spring (not shown) in the proximal direction. The piston-rod guide 17 serves for enabling that the piston rod 13, after the replacement of a cartridge, may be screwed into the upper housing part 3. Herein, the operator may grip the piston-rod guide 17 at the knurl 18, rotating the piston-rod guide 17 in relation to the housing 2. In the case of injection devices in which a replacement of the cartridge is not provided, the piston rod 13 may be held in a rotationally fixed manner directly on the upper housing part 3. In the proximal position of the piston-rod guide 17, shown in FIG. 4, the ramps 20 and 21 are disengaged such that the piston-rod guide 17 may be rotated in relation to the upper housing part 3.

As is shown in FIG. 4, the injection device 1 has a feed part 24 which in the embodiment is configured in a substantially cylindrical manner, the piston rod 13 protruding thereinto. The piston rod 13 is connected by way of a threaded connection 27 to the feed part 24. On account of the piston rod 13 being fixed in a rotationally fixed manner in the upper housing part 3, rotation of the feed part 24 causes movement of the feed part 24 in the distal direction. The feed part 24 is connected in a rotationally fixed manner by way of a longitudinal guide 32 to the operating element 6. Moreover, the injection device 1 has a setting part 25. The setting part 25 in the embodiment is likewise configured in a substantially cylindrical manner and is disposed on the external circumference of the feed part 24. The setting part 25 by way of a proximal end side 74 bears on a periphery 75 of the feed part 24. The setting part 25 is connected by way of a threaded connection 26 to the upper housing part 3. Rotation of the setting part 25 in the first rotation direction 43 (FIG. 1) by virtue of the threaded connection 26 causes movement of the setting part 25 in the distal direction, and rotation in the opposite rotation direction 44 (FIG. 6) causes movement of the setting part 25 in the proximal direction.

The setting part 25 has a web 42 which protrudes radially outward from the cylindrical portion of the setting part 25, a spring 28 being held on the web 42. The spring 28 is configured as a torsion spring and, by way of the other end thereof, is secured to the upper housing part 3. The spring 28 biases the setting part 25 in relation to the upper housing part 3, counter to the first rotation direction 43 (FIG. 1).

A coupling 33 which in FIG. 4 is located in a position 47 in which the coupling 33 is open acts between the operating element 6 and the setting part 25. In the position 47, the coupling 33 permits relative rotation of the setting part 25 in relation to the operating element 6. The coupling 33 includes a toothing 34 on the operating element 6 which in a position 46 of the coupling 33 (FIG. 5) may engage in a toothing 35 on the setting part 25 and, on account thereof, may interconnect in a rotationally fixed manner the operating element 6 and the setting part 25. As is shown in FIG. 4, the toothing 34 has a height (b) which is measured parallel to the longitudinal central axis 10. In the position shown in FIGS. 3 and 4, the operating element 6 bears on the stop 73 of the upper housing part 3.

As is also shown in FIG. 4, the operating element 6 in the axial direction is fixedly connected to a latching part 29. The latching part 29 is configured so as to be sleeve-shaped and by way of a longitudinal guide 36 is connected in a rotationally fixed manner to the upper housing part 3. The latching part 29 is biased in the distal direction by the spring 37 which in the embodiment is embodied as a compression spring. The latching part 29 has a depression 80 in which the spring 37 is disposed. The spring 37 is supported on a step 81 of the latching part 29. The depression 80 delimits a hollow-cylindrical receptacle space for the spring 37, which is configured between the latching part 29 and the setting part 25. A latching periphery 39 of the operating element 6, which protrudes into a depression 38 of the latching part 29, serves for the axially fixed connection of the operating element 6 to the latching part 29. However, it may also be provided that the operating element 6 acts on the latching part 29 only in the case of movement in the proximal direction, a movement of the latching part 29 in the distal direction, following the operating element 6, being performed by virtue of the spring 37.

The latching part 29 has an end side 50 which faces a periphery 40 of the setting part 25. The end side 50 is the distal end side of the latching part 29. A first latching element 30 of the latching part 29 is disposed on the end side 50. The first latching element 30 in the position shown in FIG. 4 has a spacing (a) from the periphery 40 which is measured in the direction of the longitudinal central axis 10. The latching element 30 is disengaged from a latching element on the setting part 25 that is not shown in FIG. 4 and that is disposed on that side of the periphery 40 that faces the end side 50. In FIG. 4, the setting part 25 and the latching part 29 are located in a second axial position 49 in which, independently of the rotational position of the setting part 25 and of the latching part 29, latching between the setting part 25 and the latching part 29 is not possible.

Figure 5:
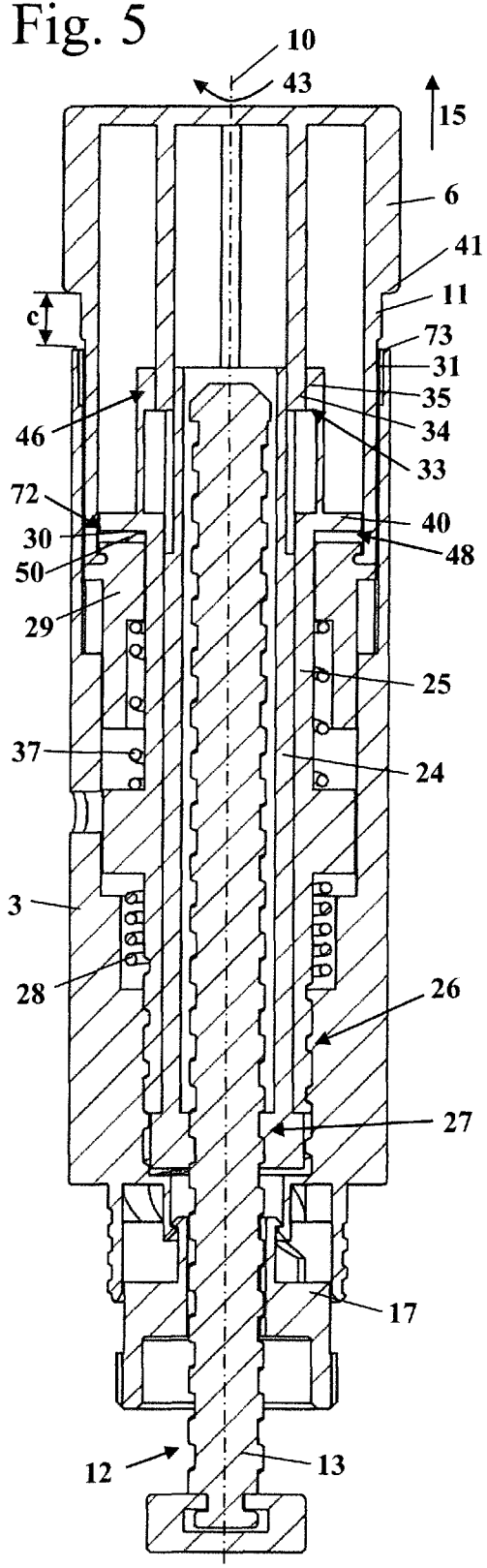
FIG. 5 shows a section along the line IV-IV in FIG. 3, in the position of the injection device according to FIG. 1.

After injection fluid has been pressed out, the operating element 6 is moved by the spring 37 from the position shown in FIG. 4 in the direction of the arrow 15, that is, in the distal direction, until the operating element 6 is located in the position shown in FIG. 5. The operating element 6 has a step 41 which in FIG. 4 bears on the stop 73 and in FIG. 5 has a spacing (c) from the stop 73. The spacing (c) corresponds to the spacing (a), shown in FIG. 4, between the latching element 30 and the periphery 40. The latching installation 72 which is formed between the setting part 25 and the latching part 29 in FIG. 5 is shown in a first axial position 48 in which the first latching element 30 may interact with a latching element which is disposed on the setting part 25 and may define latching positions of the injection device 1. The latching part 29 bears in the first axial position 48 by way of the latching element 30 thereof on the periphery 40. As is also shown in FIG. 5, the longitudinal ribs 11 on the operating element 6 are shorter than the spacing (c) such that the longitudinal ribs 11 in the position of the injection device 1 shown in FIG. 5 have left the region of the longitudinal grooves 31. During the movement of the operating element 6 in the proximal direction, the toothing 34 of the operating element 6 has been pushed into the toothing 35 of the setting part 25. In the first position 46 of the coupling 33, shown in FIG. 5, the operating element 6 and the setting part 25 are interconnected in a rotationally fixed manner.

In order for an injection dosage to be set, the operating element 6 has to be rotated in the first rotation direction 43 about the longitudinal central axis 10. The feed part 24, by virtue of the rotationally fixed connection between the operating element 6 and the feed part 24, is also rotated. Additionally, the feed part 24 moves by way of the second threaded connection 27 in the distal direction. By way of the coupling 33, the setting part 25 is likewise connected in a rotationally fixed manner to the operating element 6 and, during rotation thereof, by virtue of the threaded connection 26 likewise additionally moves in the distal direction. The distance covered by the feed part 24 and by the setting part 25 here may be of approximately equal length. The distance which is covered by the setting part 25 is preferably somewhat longer than the distance of the feed part 24, such that movement of the dosing piston 12 in the proximal direction may be avoided when a dosage is being set. The latching part 29 is moved by the spring 37 in the distal direction and trails the movement of the setting part 25. On account thereof, the operating element 6 which is fixedly connected to the latching part 29 is also moved in the distal direction.

Figure 6:
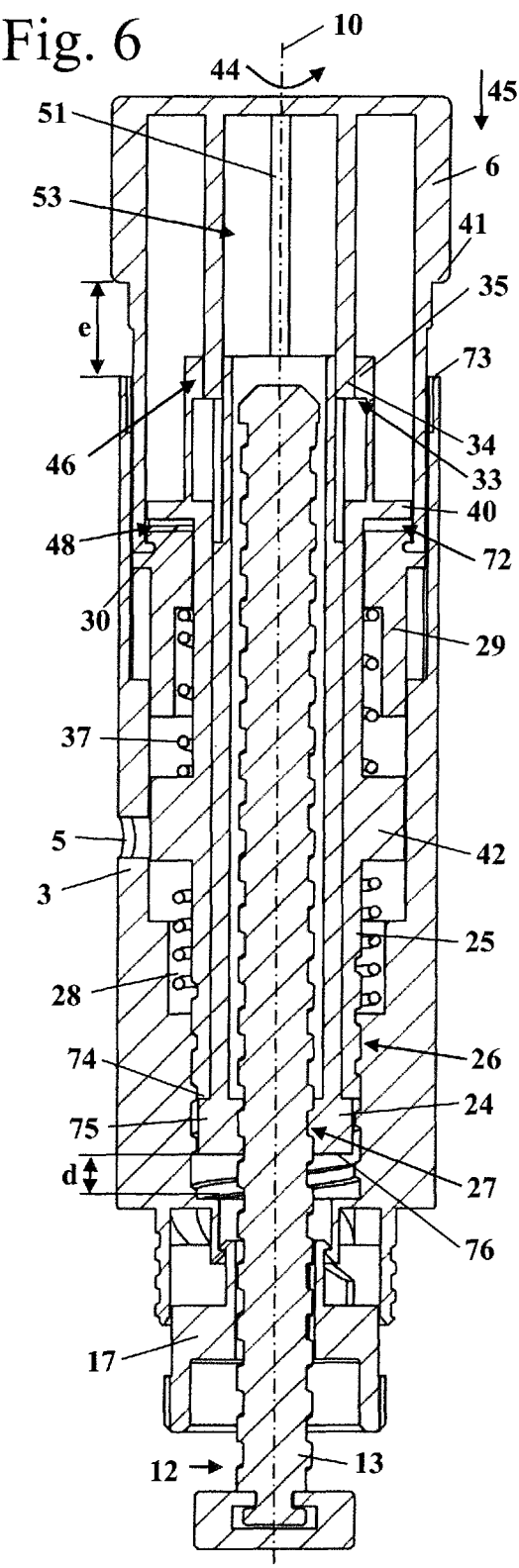
FIG. 6 shows a section along the line IV-IV in FIG. 3, in the position of the injection device according to FIG. 2.
Figure 14:
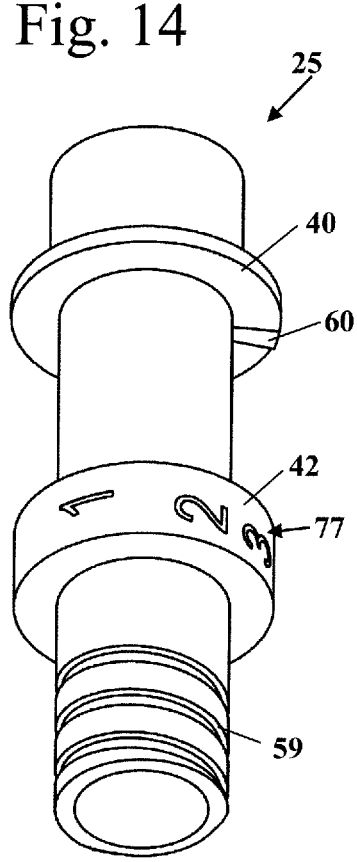
FIG. 14 shows a perspective illustration of a setting part of the injection device.

The injection device 1 after an amount of injection fluid to be dispensed has been set is shown in FIG. 6. The step 41 in relation to the stop 73 has a spacing (e) which is significantly larger than the spacing (c). The feed part 24 has a proximal end side 76 which in relation to the position shown in FIG. 5 has been moved along a distance (d) in the distal direction. The spacing (e) corresponds to the total sum of the distance (d) and of the spacing (c) shown in FIG. 5. The web 42 of the setting part 25, the graduation 77 being disposed on the external circumference thereof (FIG. 14), is visible through the clearance 5 of the housing part 3.

In order for a set amount of injection fluid to be dispensed, the operator moves the operating element 6, counter to the force of the spring 37, in the proximal direction, as is indicated by the arrow 45. On account thereof, the operating element 6 is moved relative to the setting part 25. The coupling 33 is adjusted to the second position 47 shown in FIG. 4. The latching element 30 also moves in the proximal direction in relation to the setting part 25, such that the first latching element 30 is disengaged from a latching element which is disposed on the periphery 40. The latching installation 72, by the movement of the operating element 6 in the proximal direction, is adjusted to the second axial position 49 which is shown in FIG. 4. In the embodiment, the latching installation 72 is disengaged first, the coupling 33 being subsequently released. As soon as the coupling 33 and the latching installation 72 have been released, the setting part 25 is rotated by the spring 28 in the second rotation direction 44 (FIG. 6) which is counter to the first rotation direction 43. The setting part 25 by way of the threaded connection 26, additionally to rotating in the direction of the arrow 45, moves in the proximal direction. The end side 74 of the setting part 25 acts on the periphery 75 of the feed part 24 and adjusts the feed part 24 in the proximal direction by the distance (d). Since the feed part 24 is connected in a rotationally fixed manner to the operating element 6, the feed part 24 is unable to rotate. Therefore, the dosing piston 12 which is connected in a rotationally fixed manner to the upper housing part 3 is moved in the proximal direction and presses injection fluid out of the container.

Figure 7:
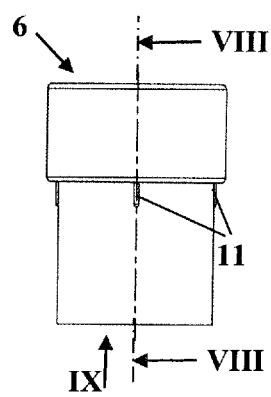
FIG. 7 shows a side view of an operating element of the injection device.
Figure 8:
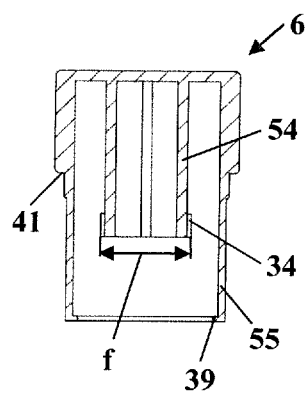
FIG. 8 shows a section along the line VIII-VIII in FIG. 7.
Figure 9:
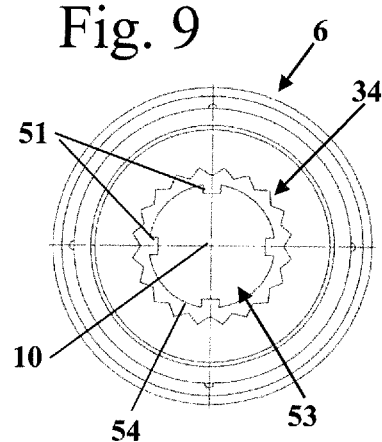
FIG. 9 shows a view from below of the operating element, in the direction of the arrow IX in FIG. 7.
Figure 10:
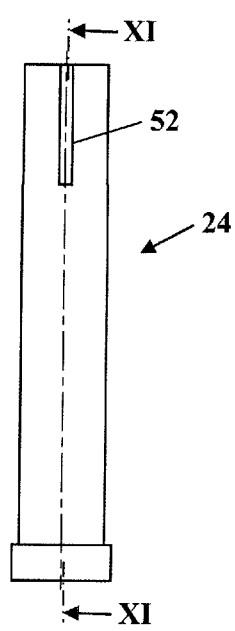
FIG. 10 shows a side view of a feed part of the injection device.

The parts of the injection device 1 are shown in detail in FIGS. 7 to 26. FIGS. 7 to 9 show the operating element 6. The longitudinal ribs 11 on the operating element 6 are shown in FIG. 7. Four longitudinal ribs 11 which are disposed so as to be uniformly distributed on the circumference are provided in the embodiment.

As is shown in FIGS. 8 and 9, the operating element 6 is configured in an approximately cylindrical manner and has a sleeve 55, the inwardly protruding latching periphery 39 being disposed on the proximal end thereof. The sleeve 55 at the distal end thereof is closed. An approximately cylindrical port 54 which lies completely within the sleeve 55 and on the proximal side of which the toothing 34 is configured is attached within the sleeve 55. In the embodiment, the toothing 34 is configured on the external side of the port 54. The toothing 34 has an external diameter (f). As is also shown in FIGS. 8 and 9, webs 51, which interact with grooves 52 on the external circumference of the feed part 24, shown in FIGS. 10 and 11, and in any relative position of the operating element 6 interconnect in a rotationally fixed manner the operating element 6 and the feed part 24, are provided on the internal circumference of the port 54. As is shown in FIGS. 6 and 9, the port 54 delimits a receptacle 53 into which the feed part 24 protrudes.

Figure 11:
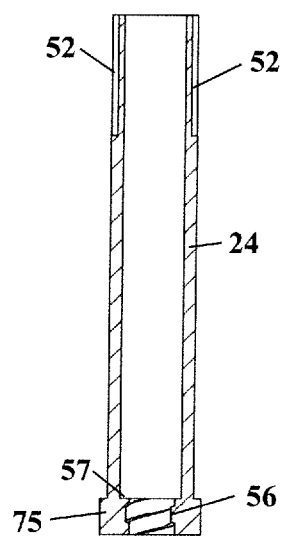
FIG. 11 shows a section along the line XI-XI in FIG. 10.
Figure 12:
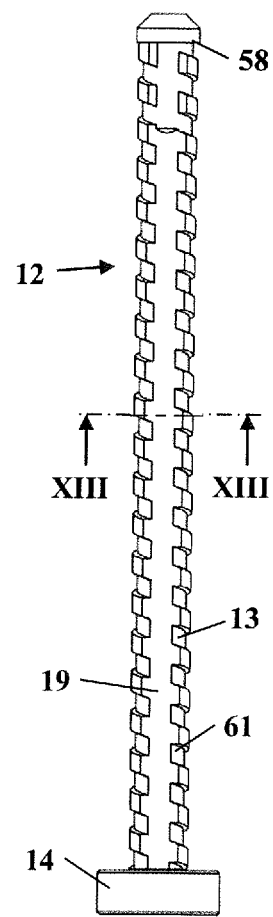
FIG. 12 shows a side view of a dosing piston of the injection device.
Figure 13:
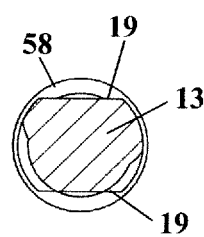
FIG. 13 shows a section along the line XIII-XIII in FIG. 12.

As is shown in FIG. 11, the feed part 24 in the region of the periphery 75 has an internal thread 56. The piston rod 13 has an external thread 61, shown in FIG. 12, which is screwed into the internal thread 56 of the feed part 24. A step 57 on which a stop 58 of the piston rod 13 impacts when a dosage is being set which is larger than the residual amount present in the cartridge is disposed on the periphery 75. The stop 58 is disposed on the distal end of the piston rod 13 and has a larger external diameter than the external thread 61 of the piston rod 13. In order to permit assembly of the piston rod 13 on the feed part 24, the piston disk 14 is configured so as to be separate from the piston rod 13, and is fastened to the latter. As is shown in FIG. 13, the piston rod 13 has two bevels 19 which are disposed on mutually opposite longitudinal sides of the piston rod 13 and which serve for the rotationally fixed connection to the piston-rod guide 17. However, any other configuration of the rotationally fixed connection may also be advantageous.

Figure 15:
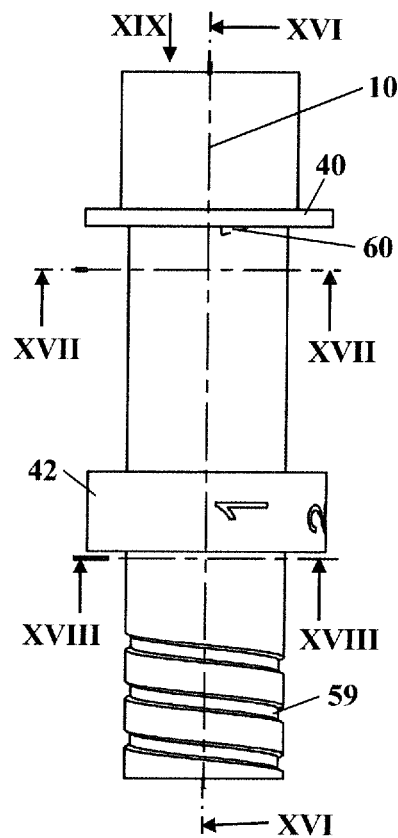
FIG. 15 shows a side view of the setting part of FIG. 14.

The configuration of the setting part 25 is shown in detail in FIGS. 14 to 19. The setting part 25 is also configured so as to be approximately sleeve-shaped and has the outwardly projecting periphery 40, on the proximal side of which a second latching element 60 is disposed. The second latching element 60 interacts with latching elements on the latching part 29, forming with the latter the latching installation 72. The latching element 60 is schematically shown in a side view in FIG. 15. In FIG. 15, the latching element 60 is located behind the drawing plane. The latching element 60 is configured so as to be ramp-shaped, wherein the flank of the latching element 60, which runs approximately parallel to the longitudinal central axis 10, in the case of rotation of the setting part 25 in the second rotation direction 44, is disposed so as to be leading, and the flank with a flat slope, in the case of rotation of the setting part 25 in the first rotation direction 43, is disposed so as to be leading. An external thread 59 which is part of the first threaded connection 26 is provided in the proximal region of the feed part 24.

Figure 16:
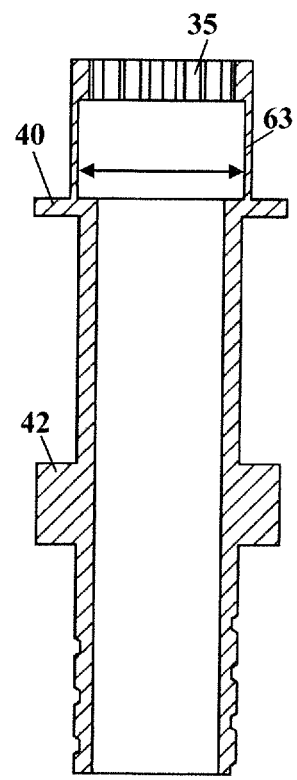
FIG. 16 shows a section along the line XVI-XVI in FIG. 15.
Figure 19:
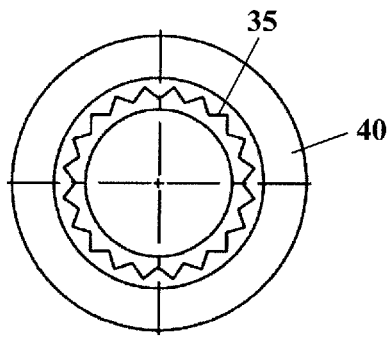
FIG. 19 shows a side view in the direction of the arrow XIX in FIG. 15.
Figure 20:
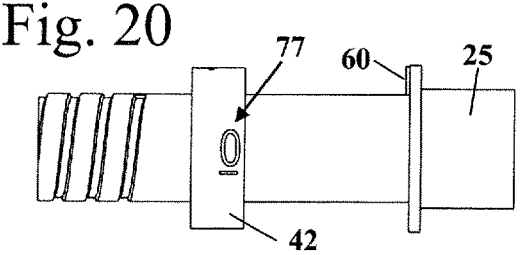
FIGS. 20 to 23 show side views of the setting part of FIG. 14.
Figure 21:
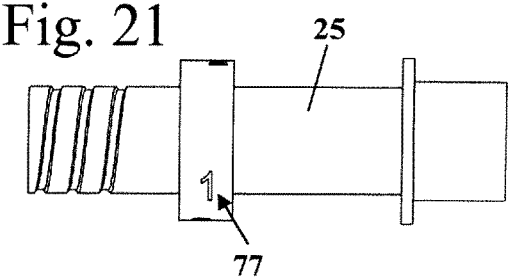
Figure 22:
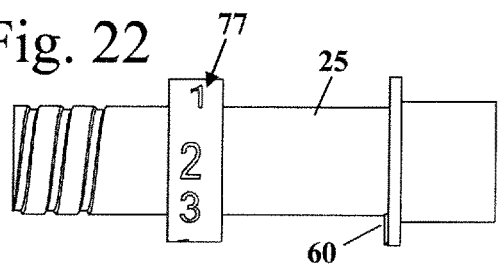
Figure 23:
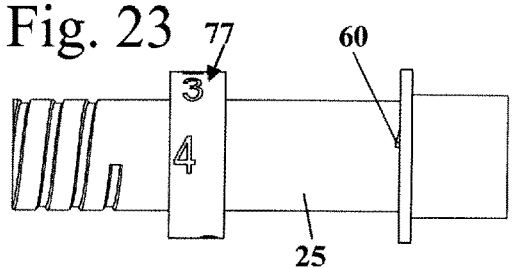

As is shown in FIGS. 16 and 19, the toothing 35 of the coupling 33 is disposed on the distal side of the setting part 25, so as to face inward. The proximal side of the toothing 35 is adjoined by a sleeve-shaped portion 63 of the setting part 25, the internal diameter (g) thereof being larger than the external diameter (f) of the toothing 34 shown in FIG. 8. As soon as the toothing 34 is located in the sleeve-shaped portion 63, the toothings 34 and 35 are disengaged, the operating element 6 being rotatable in relation to the feed part 24.

Figure 17:
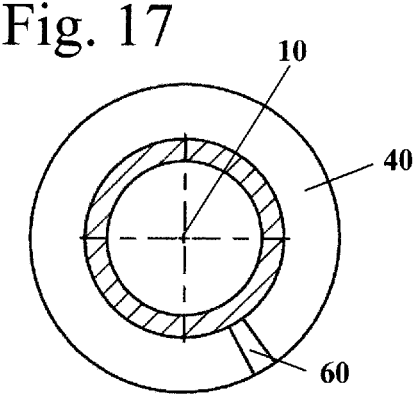
FIG. 17 shows a section along the line XVII-XVII in FIG. 15.
Figure 18:
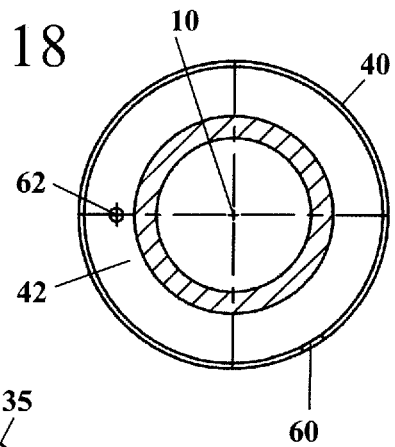
FIG. 18 shows a section along the line XVIII-XVIII in FIG. 15.

As is shown in FIG. 17, the second latching element 60 extends across the entire width of the periphery 40, measured in the radial direction to the longitudinal central axis 10. A single second latching element 60 is provided in the embodiment. However, another number of second latching elements 60 may also be advantageous, for example when only a minor angle of rotation of the operating element 6 is required, and when it is desirable for the latching positions to be clearly perceptible and audible. As is shown in FIG. 18, the web 42 has an opening 62. The spring 28 is hooked into the opening 62.

The graduation 77 which is applied to the web 42 of the setting part 25 is shown in detail in FIGS. 20 to 23. The individual values on the graduation 77 in the circumferential direction have dissimilar mutual spacings. The amount of lateral offset between the values, that is, the offset in the direction of the longitudinal central axis 10 (FIG. 15), is also dissimilar. The spacings of the values in the circumferential direction, measured in each case from the center of the values of the graduation 77, correspond to the spacings of the assigned latching elements on the latching part 29. The dissimilar amount of lateral offset is a result of the axial distance which is covered by the setting part 25 from one latching position to the next latching position.

The latching part 29 is shown in detail in FIGS. 24 to 28. The latching part 29 is configured so as to be approximately sleeve-shaped, having on the end side 50 thereof the first latching elements 30, 64, 65, 66, 67 and 68. The latching element 64 is assigned to the zero position, and the first latching element 65 which in the circumferential direction is disposed at a short spacing from the latching element 64 corresponds to the position for priming. The latching elements 66, 67, 68 and 30 which are disposed at dissimilar mutual spacings correspond to different amounts of injection fluid to be set. All first latching elements 30 and 64 to 68 are configured so as to be ramp-shaped, wherein that flank which in the case of rotation of the setting part 25 in the rotation direction 43 is leading is slightly chamfered, while the trailing flank descends steeply. If and when the setting part 25 in relation to the latching part 29 is moved in the first rotation direction 43, the flank with a flat slope of the second latching element 60 slides down a flank, running at a chamfer, of one of the latching elements 30 and 64 to 68. On account thereof, a force on the latching part 29 in the proximal direction is created, leading to a deflection of the latching part 29 counter to the force of the spring 37. On account thereof, reaching a latching position is audible and perceptible to the operator.

Figure 24:
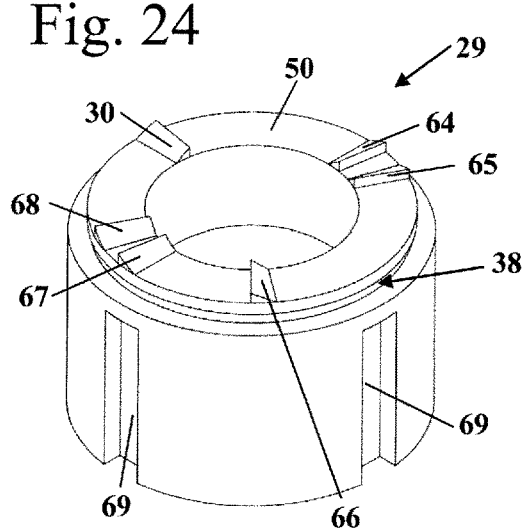
FIG. 24 shows a perspective illustration of a latching part of the injection device.
Figure 25:
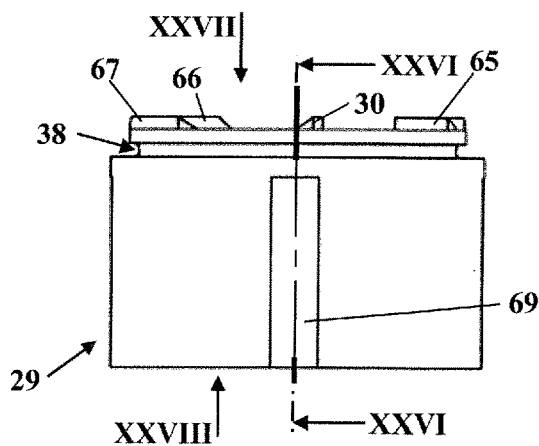
FIG. 25 shows a side view of the latching part of FIG. 22.
Figure 26:
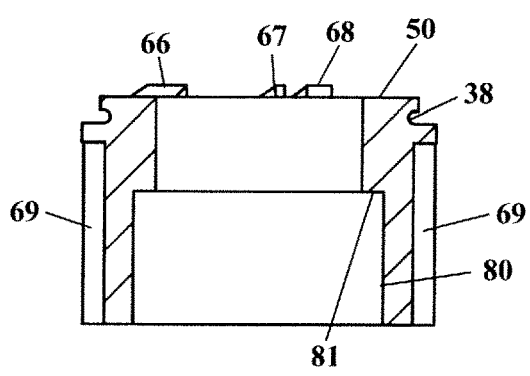
FIG. 26 shows a section along the line XXVI-XXVI in FIG. 25.
Figure 27:
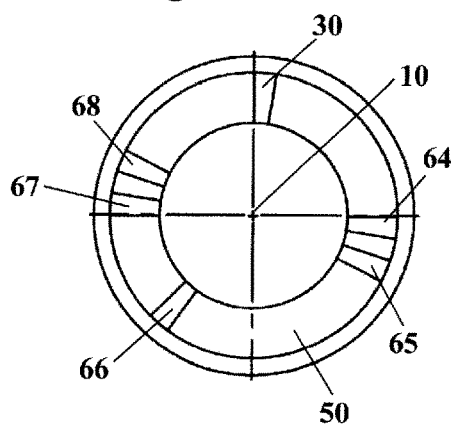
FIG. 27 shows a plan view of the latching part, in the direction of the arrow XXVII in FIG. 25.
Figure 28:
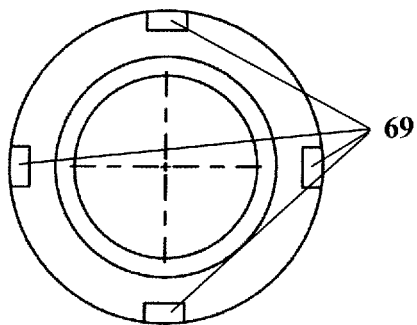
FIG. 28 shows a view from below in the direction of the arrow XXVIII in FIG. 25.

As is shown in FIGS. 24 to 26, the latching part 29, in a manner directly adjacent to the end side 50, has the depression 38 in which the latching periphery 39 of the operating element 6 engages. As is shown in FIG. 26, the latching part 29 on that side that faces away from the end side 50 has the depression 80 on which the latching part 29 has an enlarged internal diameter. The depression 80 by way of a step 81 transitions into a portion of reduced internal diameter. The depression 80, collectively with the setting part 25, delimits a receptacle space for the spring 37. The spring 37 is supported on the step 81. As is shown in FIGS. 24, 25, 26 and 28, four depressions 69 are uniformly distributed on the circumference of the latching part 29. The depressions 69 run parallel to the longitudinal central axis 10 of the injection device 1, serving for the rotationally fixed connection of the latching part 29 to the upper housing part 3. The non-uniform disposal of the first latching elements on the end side 50 is also shown in FIG. 27. The first latching elements 30 and 64 to 68 may be disposed in an almost arbitrary manner on the end side 50. Advantageously, the operating element 6, until the maximum dosage is reached, is rotatable by fewer than one full revolution. On account thereof, each latching element is passed at most once when setting the dosage, such that an arbitrary disposal of the latching elements and, on account thereof, an arbitrary selection of amounts of injection fluid to be set is possible.

Figure 29:
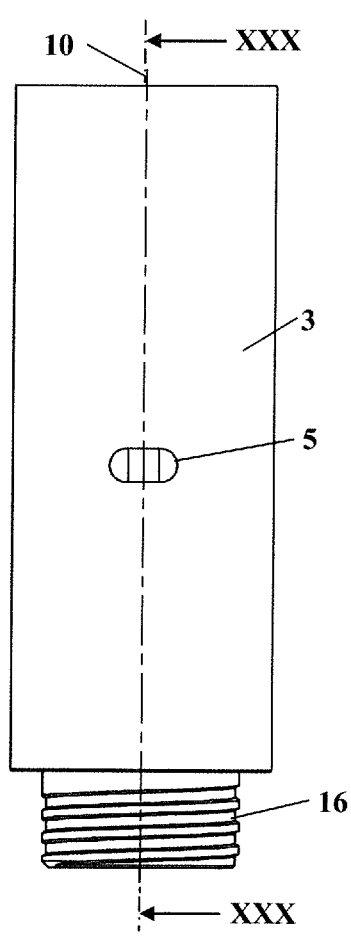
FIG. 29 shows a side view of an upper housing part of the injection device; and, FIG. 30 shows a section along the line XXX-XXX in FIG. 29.
Figure 30:
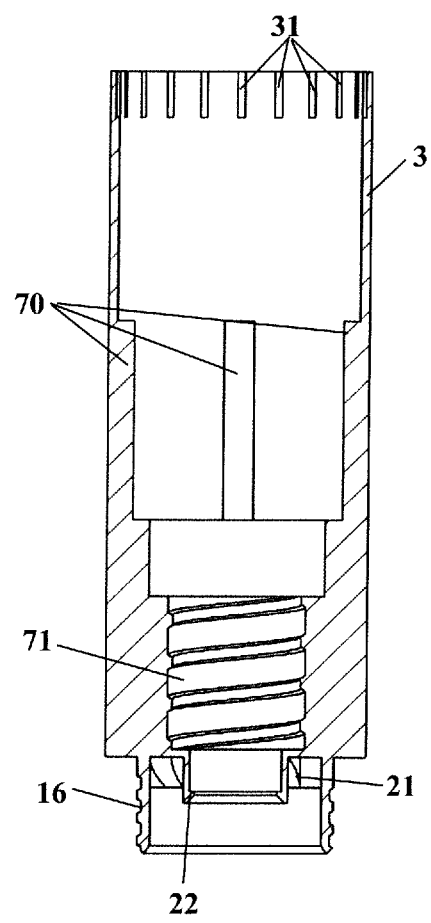

The upper housing part 3 is shown in FIGS. 29 and 30. As is shown in FIG. 29, the upper housing part 3 on the internal side thereof has longitudinal webs 70 which engage in the depressions 69 of the latching part 29 and, on account thereof, hold the latching part 29 in a rotationally fixed manner in the housing 2. The housing part 3 in the proximal region thereof has an internal thread 71 which interacts with the external thread 59 of the setting part 25 (FIG. 14), forming with the latter the first threaded connection 26. As is also shown in FIG. 26, the upper housing part 3 at the distal end thereof has a multiplicity of longitudinal grooves 31 such that the operating element 6 in various rotational positions may be pushed into the housing part 3.

On account of the setting part 25 rotating in relation to the housing 2 when setting the amount of injection fluid to be dispensed, and rotating back by the same distance when the dosage is being pressed out, the setting part 25 and the latching part 29, which is held in a rotationally fixed manner on the housing 2, in each latching position are located in an unequivocally defined mutual rotational position. Since the rotational position of the setting part, in the case of a setting part which when setting a dosage for injection covers at maximum one full revolution, at all times corresponds to one dosage for injection, a separate latching position may be provided for each dosage. Intermediate latching increments are not required.

It is understood that the foregoing description is that of the preferred embodiments of the invention and that various changes and modifications may be made thereto without departing from the spirit and scope of the invention as defined in the appended claims.

What is claimed is:

1. An injection device defining a longitudinal center axis, the injection device comprising:
    a housing;
    a setting part configured to, in relation to said housing, rotate in a first rotational direction when an amount of injection fluid to be dispensed is being set;
    said setting part being further configured to rotate in a second rotational direction counter to said first rotational direction when said injection fluid is being pressed out of the injection device;
    a latching unit defining at least one latching position of said setting part and configured to act between said setting part and said housing;
    said latching unit being configured to be active at least when said amount of injection fluid to be dispensed is being set;
    each of said at least one latching positions having an unequivocal rotational position of said setting part in relation to said housing assigned thereto;
    said injection device defining a proximal direction and a distal direction;
    said setting part being directly connected to said housing via a first threaded connection; and,
    said setting part being further configured to move in the distal direction in addition to rotating in said first rotational direction when said amount of injection fluid to be dispensed is being set and to move in the proximal direction in addition to rotating in said second rotational direction when said amount of injection fluid is being pressed out.

2. The injection device of claim 1 further comprising:
    a first latching element connected to said housing in a rotatably fixed manner;
    a second latching element connected to said setting part in a rotatably fixed manner and configured to coact with said first latching element; and,
    said first latching element and said second latching element conjointly defining said at least one latching position.

3. The injection device of claim 2, wherein:
    said latching unit includes a latching part;
    said latching part is configured to be displaceable in an axial direction along the longitudinal center axis independently of said setting part;
    said latching part is connected to said housing in a rotationally fixed manner;
    said first latching element is arranged on said latching part; and,
    said first latching element and said second latching element conjointly define said at least one latching position in a first axial position of said latching part and said setting part and are disengaged in a second axial position of said latching part and said setting part independently of the rotational position of said setting part in relation to said latching part.

4. The injection device of claim 3 further comprising a spring configured to bias said latching part in the direction toward said first axial position.

5. The injection device of claim 2, wherein said first latching element is configured to be deflected in an axial direction along the longitudinal center axis prior to reaching a latching position.

6. The injection device of claim 1, wherein:
    said latching unit is configured to, in each of said at least one latching position, permit a relative rotation of said setting part in relation to said housing in said first rotational direction and to block a relative rotation of said setting part in relation to said housing in said second rotational direction.

7. The injection device of claim 1 further comprising a spring configured to act between said setting part and said housing and to bias said setting part in said second rotational direction.

8. The injection device of claim 1 further comprising:
    a coupling defining a first coupling position and a second coupling position;
    an operating element; and,
    said coupling being configured to connect said setting part to said operating element in a rotationally fixed manner in said first coupling position and to permit relative rotation of said setting part in relation to said operating element in said second coupling position.

9. The injection device of claim 8, wherein said injection device defines a proximal direction and said coupling is configured to be adjusted from said first coupling position to said second coupling position via a displacement of said operating element in the proximal direction.

10. The injection device of claim 8, wherein:
    said injection device defines a proximal direction;
    said latching unit includes a latching part coupled to said operating element in axial direction; and,
    said operating element being configured such that a movement of said operating element in said proximal direction causes said latching part to move in said proximal direction.

11. The injection device of claim 8, wherein said latching unit and said operating element are interconnected in an axially fixed manner and so as to be rotatable in relation to each other.

12. The injection device of claim 8, wherein:
    said coupling has a first toothing on said setting part;
    said operating element has a second toothing; and,
    said first toothing is configured to interact with said second toothing.

13. The injection device of claim 8 further comprising:
    a feed part;
    a dosing piston held in a rotationally fixed manner in relation to said housing;
    said operating element is connected to said feed part in a rotationally fixed manner; and,
    said feed part is connected to said dosing piston via a second threaded connection.

14. The injection device of claim 13, wherein said setting part is configured to act on said feed part such that a movement of said setting part in the proximal direction causes a movement of said feed part in the proximal direction.

* * * * *